United States Patent [19]

Dodin et al.

[11] Patent Number: 4,677,055

[45] Date of Patent: Jun. 30, 1987

[54] IMMUNOLOGICAL DETECTION OF BACTERIAL PATHOGENS WITH ANTIBODY-CONTAINING MAGNETIC GEL

[75] Inventors: André Dodin; Eustrate Avrameas; Bruno Goud, all of Paris; Michel Guillou, Les Clayes-sous-Bois; Reneé Nicolas, Malakoff, all of France

[73] Assignee: Institut Pasteur, Paris, France

[21] Appl. No.: 558,895

[22] Filed: Dec. 7, 1983

[30] Foreign Application Priority Data

Dec. 9, 1982 [FR] France .................. 82 20632

[51] Int. Cl.⁴ ............... G01N 33/549; G01N 33/553; G01N 33/554; G01N 33/559
[52] U.S. Cl. ........................................ 435/7; 435/4; 435/29; 435/34; 435/810; 436/515; 436/526; 436/530; 436/535; 436/808
[58] Field of Search ............. 435/29, 34, 4, 7, 810; 436/515, 526, 530, 808, 535

[56] References Cited

U.S. PATENT DOCUMENTS

| | | |
|---|---|---|
| 3,674,438 | 7/1972 | Shen .................. 436/515 X |
| 3,981,776 | 9/1976 | Saxholm ............. 436/515 X |
| 4,115,534 | 9/1978 | Ithakissios ......... 436/526 X |
| 4,241,176 | 12/1980 | Avrameas et al. ........ 435/7 |
| 4,272,510 | 6/1981 | Smith ................ 436/526 X |
| 4,352,880 | 10/1982 | Awerbuch ............ 435/29 X |

OTHER PUBLICATIONS

Chemical Abstracts, 93: 3332r (1980).
INSERM, Jun. 1979, vol. 86, pp. 137–146, Guesdon et al, The Use of Antigens and Antibodies Immobilized on Magnetic Supports in Immunological Procedures.

*Primary Examiner*—Sidney Marantz
*Attorney, Agent, or Firm*—Oblon, Fisher Spivak, McClelland, & Maier

[57] ABSTRACT

A process for the immunobacteriological detection of pathogenic germs possessing specific antigenic determinants, and a kit for carrying out the process, with the aid of a magnetic gel to which are coupled anti-specific antigenic determinant antibodies, characterized by the following steps:

(a) a biological medium supposedly contaminated by a pathogenic germ possessing a specific antigenic determinant is brought into contact with particles of the magnetic gel,
(b) the particles of magnetic gel are then removed by magnetic means and
(c) are inoculated onto a nutrient agar medium,
(d) the agar medium is incubated to develop culture colonies of the pathogenic germs;
(e) areas containing serum containing antibodies specific to the pathogenic germ to be detected are formed in the agar,
(f) the germs are lysed by means of lysing agents,
(g) the lysate is incubated with the serum for a time enabling the serological antibody-antigen reaction to take place by immunodiffusion on the agar, and
(h) the quantity of germs contained in the biological medium is read directly, by virtue of the antigen-antibody reaction on the agar.

21 Claims, No Drawings

# IMMUNOLOGICAL DETECTION OF BACTERIAL PATHOGENS WITH ANTIBODY-CONTAINING MAGNETIC GEL

FIELD OF THE INVENTION

The present invention relates to a new process for the immunobacteriological detection of pathogenic germs possessing specific antigenic determinants, such as, in particular, the fraction 1+2 defined in ANVAR French Pat. No. 73/03,734 (French Patent Publication No. 2,215,945), in contaminated biological media, and especially to a process for the immunobacteriological detection of pathogenic germs possessing a fraction 1+2, such as *Vibrio cholerae, Salmonella typhimurium, Malleomyces mallei* or *Pseudomonas pseudomallei*, in contaminated biological media, in particular in stools, blood, urine, water and excretions of all kinds.

The expression "antigenic determinants" is understood as meaning any fractions originating from a pathogenic agent and able to induce a polyspecific or monoclonal antibody capable of recognizing the said pathogenic agent.

PRIOR ART

Antigenic fractions 1+2 are known from ANVAR French Pat. No. 73/03734 of Feb. 2, 1973 and its first and second Certificates of Addition, No. 74/06,983 of Mar. 1, 1974 (French Patent Publication No. 2,262,533) and No. 77/12,152 of April 22, 1977 (French Patent Publication No. 2,388,049).

Furthermore, French Pat. No. 75/36,889 (French Patent Publication No. 2,334,106) in the name of the Institut Pasteur has disclosed a magnetic gel which can be used for immunoenzymatic determinations and which consists of an acrylamide/agarose gel containing magnetic particles and coupled to a protein, such as an antigen or an antibody, via a coupling agent, such as glutaraldehyde, this type of gel coupled to an antigen or an antibody being used for the immunoenzymatic determination of the corresponding antibody or antigen present in a biological liquid, this gel being incubated with the biological liquid, then washed several times and separated off with the aid of a magnetic field, and then incubated with antibodies or antigens labeled with an enzyme commonly used in immunoenzymatic determination, such as glucose oxidase or peroxidase, and the enzymatic activity of the gel being measured by reading the optical density.

French Pat. No. 79/21,343 (French Patent Publication No. 2,463,807) in the name of the Institut Pasteur and ANVAR proposes a process for fixing biological protein molecules, such as antigens, antibodies, enzymes, viruses, cells, etc., to particles of magnetic vinylaromatic polymers by adsorption, the biological molecules simply being brought into contact, in a suitable buffer, with beads of the abovementioned magnetic polymers for 1 hour at 37° C. and overnight at 4° C.

Furthermore, Institut Pasteur and C.N.R.S. French Patent Application No. 81/18,985 (French Patent Publication No. 2,514,367) of Oct. 8, 1981 discloses a process for the detection of pathogenic germs in fluids, in particular in supply water, by filtration on an immunoadsorbent consisting of an insoluble support and more particularly an insoluble polymer such as a gel, especially a gel of polyacrylamide and/or of agarose, to which antibodies specific for the pathogenic germ whose presence in a fluid it is desired to determine are fixed by chemical bonding, in particular antibodies inhibiting fraction Ch 1+2 of *Vibrion cholerae*, antibodies inhibiting *Salmonella typhimurium*, antibodies inhibiting type I and II poliomyelitis virus, antibodies inhibiting *Escherichia coli* or antibodies inhibiting encephalomyocarditis virus, this filtration being followed by characterization of the antigenic factors retained by the immunoadsorbent, this characterization being carried out by conventional means such as dilution of the gel and culture on agar in a selective liquid medium, biochemical and serological characterization of the germ (agglutination), etc.

SUMMARY OF THE INVENTION

The object of the present invention is to isolate the pathogenic germ from the unknown contaminated biological medium directly on beads of magnetic gel to which an antibody is fixed, the germ being concentrated by these beads into quantities very much greater than the low concentrations of germs initially present in a biological medium. This makes it possible to diagnose not only the disease but also the presence of pathogenic germs in a carrier of small quantities of these germs, and to characterize the pathogenic germ in less than 48 hours in immunodiffusion, and also to diagnose the possible presence of several pathogenic germs in one and the same biological medium, thus affording a considerable saving in terms of the quantity of medium to be tested and in terms of time, since several germs can be detected simultaneously by the process forming the subject of the present invention, which process, moreover, does not require the use of selective culture media.

The present invention relates to a process for the immunobacteriological detection of pathogenic germs possessing specific antigenic determinants, such as, in particular, the antigenic fraction 1+2, in contaminated biological media, with the aid of a magnetic gel to which antibodies inhibiting the specific antigenic determinants are fixed, that is, anti-specific antigenic determinant antibodies in which process a biological medium supposedly contaminated by a pathogenic germ possessing the said specific antigenic determinant, such as, for example, the fraction 1+2, is brought into contact with particles that is, beads, or the like, of the said magnetic gel for a sufficient time to permit the fixing to the gel of the germs contained in the biological medium, the beads, or the like, of magnetic gel are removed from the mixture by magnetic means and inoculated onto a suitable agar medium, on which they are incubated for a suitable time at a suitable temperature, wells are then scooped out in the agar, in the vicinity of the magnetic beads covered with culture colonies, embedded in the agar, and filled with a suitable serum inhibiting the pathogenic germ to be detected, that is, a serum containing antibodies specific to said pathogenic germ, the germs are lyzed by means of suitable lyzing agents, the lyzate is incubated with the serum for a time suitable for enabling the serological antibody-antigen reaction to take place by immunodiffusion on the agar, and the quantity of germs contained in the biological medium is read directly, by virtue of the antigen-antibody reaction on the agar.

In an advantageous embodiment of the immunobacteriological detection process according to the present invention, applied to the simultaneous detection of several pathogenic germs in a biological medium, the wells scooped out in the agar are filled with different sera inhibiting the pathogenic germs.

In another advantageous embodiment of the process according to the invention, the antibodies inhibiting the specific antigenic determinants, fixed to the beads, or the like, of magnetic gel, are antibodies inhibiting fraction 1+2, originating from a hyperimmune serum inhibiting fraction 1+2, and obtained, according to French Pat. No. 73/03, 734 or one of its Additions No. 74/06,983 or 77/12,152, by extraction of the IgG from the said hyperimmune serum.

In an advantageous variant of this embodiment, for applying the process according to the invention to the simultaneous detection of several pathogenic germs in a biological medium, series of beads, or the like, of magnetic gel, each of which has fixed to it antibodies inhibiting fraction 1+2, originating from cultures of each of the pathogenic germs to be detected, are brought into contact with the biological medium.

According to the invention, the serum inhibiting the pathogenic germ, introduced into the wells scooped out in the agar, is chosen from the group comprising sera specific for germs inhibiting fraction 1+2, polyvalent sera inhibiting pathogenic germs possessing a fraction 1+2, sera inhibiting the toxin of the pathogenic germ, and sera inhibiting sub-unit A or B of the said pathogenic germs.

In an advantageous embodiment of the process according to the invention, the biological medium to which the process is applied is chosen from the group comprising stools, blood, urine, excretions of all kinds, and water.

In another advantageous embodiment of the process according to the invention, the magnetic means used to remove the beads, or the like, of magnetic gel from the biological medium, after incubation with the latter, consist of a magnetized rod.

In yet another advantageous embodiment of the process according to the invention, the agent for lyzing the germs cultured on the beads embedded in the agar is a chemical lyzing agent such as toluene, a "Tween"—which is a condensation product of ethylene oxide with a "Span" detergent formed from fatty acid esters and sorbitol—or glucose at high concentration, in particular, or an enzymatic lyzing agent such as, for example, complement.

In an advantageous embodiment of the process according to the invention, the beads, or the like, of magnetic gel attached to the magnetic means are washed several times before being inoculated onto the agar.

In another advantageous embodiment of the process according to the invention, the beads, or the like, of magnetic gel attached to the magnetic means are detached from the latter by the action of a magnetic field in order to be inoculated onto the agar.

Antigenic fraction 1+2 is defined according to ANVAR French patent specification No. 73/03734, published as Pat. No. 2,215,945, as the antigen fraction obtained from a germ culture of *Vibrio cholerae, Salmonella typhi murium, Malleomyces mallei* or *Pseudomonas mallei,* which fraction is the portion of the pathogenic germ culture which gives the first peak on the ultraviolet absorption diagram at 280 nm and which, facing an immunoserum produced in an animal from the same culture, gives the precipitation band (or pair of bands) closest to the antigen cup in the diffusion test in the gelose medium and in the immunoelectrophoretic analysis test, and which is the first fraction possessing the above properties emerging from a chromatograph column formed of dextran in grains of 40 to 120 microns, in the chromatography of germ culture which has been lysed to release their endocellular production.

According to the invention, the contact time between the beads of magnetic gel to which antibodies inhibiting the specific determinants are fixed and the unknown biological medium is about 2 hours at ambient temperature; the culture time on agar of the germs fixed to these beads of magnetic gel is of the order of 14 to 18 hours at 37° C.±1° C. and the reaction time of the antibodies of the serum contained in the wells inhibiting fraction 1+2 with the antigens, by immunodiffusion, is of the order of 14 to 18 hours at ambient temperature.

The present invention also relates to a ready-to-use kit for carrying out the process for the immunobacteriological detection of pathogenic germs possessing antigenic determinants, such as fraction 1+2, in contaminated biological media, the said process having been defined above, which kit comprises (in particular in the case of fraction 1+2):

a receptacle containing a suitable quantity of beads of magnetic gel to which an antibody inhibiting fraction 1+2 is fixed, a magnetized rod or the like, a culture dish, such as, in particular, a Petri dish, the bottom of which is provided with a very powerful magnet in the center of its outer face, a receptacle containing a suitable quantity of agar medium for the culture of pathogenic germs possessing a fraction 1+2, a receptacle containing a suitable quantity of serum inhibiting the pathogenic germ to be detected, a receptacle containing a suitable quantity of agents for lyzing the cultures of pathogenic germs on agar, and a receptacle containing a suitable quantity of buffered physiological wash water.

In an advantageous embodiment of the ready-to-use kit, which can be applied to the simultaneous detection of several pathogenic germs in a biological medium, the kit comprises several receptacles each containing a suitable quantity of beads of magnetic gel to which different antibodies inhibiting fraction 1+2 are fixed, and several receptacles each containing a serum inhibiting the pathogenic germ to be detected, corresponding to each of the different antibodies.

In another advantageous embodiment of the ready-to-use kit according to the invention, the magnetized rod or the like is a magnetized rod coated with "Teflon" or with another similar insulating material.

In yet another advantageous embodiment of the ready-to-use kit according to the invention, the magnetized rod or the like consists of a magnetized device such as the device forming the subject of French Patent Application No. 83/17,166 in the name of the Institut Pasteur.

In a preferred method of putting the invention into effect, the immunobacteriological detection of pathogenic germs possessing a fraction 1+2, in a contaminated biological medium, is carried out in the following manner:

(1) Beads of "Act. Magnogel AcA 44" magnetic gel are used, which are produced by IBF, contain 4% of polyacrylamide, 4% of agarose and 7% of $Fe_3O_4$, have a diameter of 60 to 140 μm and have a coupling capacity for the IgG of 2 to 4 mg/ml.

(2) IgG are fixed which have been extracted from a hyperimmune serum inhibiting fraction 1+2, obtained, by OUDIN's immunization technique, by injecting a rabbit with an antigenic fraction 1+2 obtained according to the provisions of ANVAR French Pat. No. 73/03,734 or one of its Certificates of Addition No. 74/06,983 or 77/12,152, i.e. by separation, by centrifugation, of Gram-negative germs cultured in suitable culture media, extraction of the endocellular endogenic fractions by lysis of the germs under sterile conditions (either by freezing-thawing or by ultrasound), and then separation of the antigenic fraction 1+2 by gel chromatography; or by lysis of the germs by Gallut's method and purification of the antigenic fraction 1+2 with chloroacetic acid; or by autoclaving of the culture broth, followed by centrifugation and by dialysis of the supernatant against distilled water.

The fixing of the IgG to the beads of magnetic gel is carried out either by chemical coupling with the aid of glutaraldehyde, according to Institut Pasteur French Pat. No. 75/36,889, or by adsorption, according to Institut Pasteur and ANVAR French Pat. No. 79/21,343.

The IgG fixed to the beads of magnetic gel are either identical on all the beads if it is intended to detect the presence of one pathogenic germ, or different if it is intended to detect several pathogenic germs in one and the same biological medium.

(3) The beads of magnetic gel to which 2 to 4% of antibodies inhibiting fraction 1+2 are fixed are brought into contact, for about 2 hours at the laboratory temperature, with a contaminated biological medium in solution, such as water, stools, blood, urine or other excretions.

(4) An appropriately insulated, magnetized rod of about 12 mm in diameter, such as a magnetized rod coated with "Teflon" or the magnetized device according to Institut Pasteur Pat. No. 83/17,166, is immersed in the solution with slow manual stirring; the magnetic beads attach themselves to the rod. They are washed three times in 250 ml of physiological water buffered to pH 7.4.

(5) After the third washing, the magnetic beads concentrated on the underside of the rod are inoculated onto a commercial agar medium, for example a 1.5% PASTEUR agar medium ("Agar Noble", Difco) or a MÜLLER-HINTON medium, contained in a Petri dish under which a very powerful magnet is located substantially along the axis of the dish; the magnetized rod loaded with beads is placed at the center of the Petri dish, in contact with the agar; under the action of the magnetic field created by the magnet placed under the dish, the beads detach from the rod and become embedded in the agar, on which they form a spot of about 1 cm in diameter. The Petri dish is incubated for about 14 to 18 hours at 37° C.±1° C.

If desired, germs can also be removed from these colonies using an ansa, for the purpose of carrying out conventional bacteriology.

(6) At the end of the incubation period, 3 or 4 holes are scooped out, using a sterile cutter, about 1 cm from the spot of magnetic beads covered with colonies. One microdrop of agar is run into the bottom of each of the wells in order to block it, and the wells are then filled with serum specific for the pathogenic germ inhibiting fraction 1+2, or polyvalent serum inhibiting the pathogenic germ to be detected, or serum inhibiting the complete toxin of the pathogenic germ to be detected, or serum inhibiting sub-unit A or B of the toxin of the pathogenic germ to be detected.

As a variant, each of the wells is filled with sera corresponding to different pathogenic germs, if the magnetic beads themselves carry different antibodies inhibiting fraction 1+2, in order to make it possible to detect several pathogenic germs in one and the same biological medium. The sera used are obtained by OUDIN's method from cultures of Gram-negative pathogenic germs possessing an antigenic fraction 1+2, such as *Vibrio cholerae, Salmonella typhimurium, Malleomyces mallei, Pseudomonas mallei* (or Whitmore's bacillus), *Pseudomonas pseudomallei, Legionellea pneumophila, Escherichia coli* or LT toxin, in particular, in the same way as the IgG fixed to the beads of magnetic gel are extracted from sera of the abovementioned pathogenic germs.

(7) One drop of a chemical lyzing agent such as toluene or a "Tween"—or glucose if the IgG fixed are IgG inhibiting fraction 1+2 of Vibrio cholerae—, or an enzymatic lyzing agent such as complement, is deposited on the magnetic beads covered with colonies.

(8) The Petri dish is closed to prevent any evaporation of its contents, and kept for 14 to 18 hours at ambient temperature in order to allow the serological antigen-antibody reaction to take place by immunodiffusion in the agar.

After this incubation period has elapsed, the antigens of the pathogenic germ are seen on the agar as one or more precipitation bands against the corresponding serum: thus, the antigens of *Vibria cholerae* are seen as a single precipitation band against the specific serum inhibiting fraction Ch 1+2, or as 4 or 5 bands against the polyvalent anticholera serum. The nontoxinogenic strains do not show bands corresponding to inhibition of the toxin or inhibition of the sub-unit of the toxin. The toxinogenic strains are seen as a precipitation band against the serum inhibiting the toxin or the sera inhibiting sub-units A and B of the toxin.

Compared with the method recommended by the World Health Organization, which only makes it possible to identify the pathogenic germ without enabling its toxinogenic character to be recognized, the process for the detection of pathogenic germs according to the invention has the very great advantage of enabling a toxinogenic germ to be detected.

In the case of *Vibrio cholerae*, for example, the process according to the invention makes it possible to evaluate quantities of vibrions ranging from $10^2/100$ ml (as for germ carriers) to $10^6$/ml (as for patients) and, in the case of *Escherichia coli*, the quantities evaluated can be $10^2/1000$ ml (germ carriers).

Apart from the foregoing provisions, the invention also includes other provisions, which will become apparent from the description which now follows.

The invention will be understood more clearly with the aid of the additional description which now follows, referring to examples of embodiment of the process forming the subject of the present invention.

It must be clearly understood, however, that these examples of embodiment are given solely by way of illustration of the subject of the invention and that they in no way imply a limitation thereof.

EXAMPLE 1

Detection of germs of *Vibrio cholerae* in a germ carrier (1) The biological medium taken as the starting material consists of stools supposedly contaminated by El Tor Vibrio cholerae, serotype Ogawa; a 10% suspension of stools is prepared on a shaker: 10 g of stools per 100 milliliters of water. 1 ml of "Magnogel" beads, containing 2 mg per ml of antibodies inhibiting fraction Ch 1+2, is added to this suspension.

The beads are left in contact with this suspension for 2 hours at ambient temperature.

(2) A magnetized rod coated with "Teflon" and 12 mm in diameter—or the magnetized rod of the device according to Institut Pasteur French Pat. No. 83/17,166—is immersed in the suspension with slow stirring; the beads attach themselves to the rod; they are washed 3 times in 250 ml of physiological water buffered to pH 7.5.

(3) The rod, on the underside of which the beads are concentrated, is brought into contact with a 1.5% PASTEUR agar medium ("Agar Noble", Difco) contained in a Petri dish under which a very powerful magnet is located; the rod is placed at the center of the dish, along the same axis as the magnet. The beads detach and become embedded in the agar to form a spot of 1 cm in diameter.

The Petri dish is incubated for 18 hours at 37° C.

(4) At the end of this incubation period, 4 cruciform holes are scooped out in the agar, using a sterile cutter, about 1 cm from the spot of magnetic beads covered with colonies. One microdrop of agar is run into the bottom of the wells in order to block them, and the wells are filled with serum inhibiting complete cholera toxin.

(5) One drop of toluene is deposited on the magnetic beads covered with colonies, and immediately lyzes the germs.

(6) The Petri dish is closed and incubated for 18 hours at ambient temperature.

After this time, the antigens of the toxinogenic strain of *Vibrio cholerae* are seen as a precipitation band against the antitoxin serum.

EXAMPLE 2

Detection of germs of *Vibrio cholerae* in a patient

The procedure described in Example 1 above was followed and serum inhibiting fraction Ch 1+2 was placed in two wells and serum inhibiting complete cholera toxin was placed in the other two wells; $10^6$ vibrions/ml of stool solution were evaluated and it was determined that the strain was a toxinogenic strain, whereas by subjecting a sample of the same stools to the W.H.O. method, it was possible to identify the germ but not its toxinogenic character.

EXAMPLE 3

Detection of germs of Whitmore's bacillus in a germ carrier

1. The biological product, i.e. 20 g of horse dung supposedly contaminated by Whitmore's bacilli, is diluted with physiological water to a volume of about 50 ml; 0.20 ml of magnetic beads+antibodies inhibiting Whitmore type I are added. The beads are left in contact with the sample for 1 to 2 hours at the laboratory temperature.
2. After this period has elapsed, the beads are removed with a magnetized rod and then deposited at the center of a nutrient agar medium (for example Müller-Hinton's medium) contained in a Petri dish, for example. The dish is placed in an oven for 18 hours at 37° C.
3. Wells are scooped out 8 mm from the disc of culture on beads, and the specific sera inhibiting Whitmore type I are deposited in the wells.
4. The germs on the disc are lyzed with one drop of toluene.
5. After 10 to 12 hours, a precipitation band corresponding to Whitmore's bacillus antiserum—Whitmore type I antibody can be seen if the dung contained Whitmore's bacilli.
6. The antibody wells can be replaced by small discs of paper (antibiotic type) impregnated with the specific serum.
7. Results For both type I and type II, a significant concentration of the germs is obtained, which is substantially of the same order as in Example 1.

The specific immune serum only precipitates against the antigens of type I or type II Whitmore's bacillus, so that, even if the specificity of fixing is not absolute (Proteus were detected fixed to the beads), it nevertheless does not interfere with the detection.

EXAMPLE 4

Detection of germs of *Salmonella typhimurium*

Tests were carried out on stools contaminated experimentally, using the procedure described in Example 1, with bacilli of *Salmonella typhimurium.* The concentration of the Salmonellae on agar, as described in Example 1, was of the same order as for *V. cholerae.*

The antigen common to the different types of Salmonellae (A, B, C, D, E) which is seen on agar is extracted, after location and identification by means of an agar double diffusion diagram, on a column of Sephadex G200 and used to obtain the specific serum by injection into rabbits.

The diagnosis is carried out by precipitation against the specific sera.

EXAMPLE 5

Detection of germs of *Escherichia coli*

The tests were carried out on stools contaminated experimentally, following the procedure described in Example 1. The same good concentration results were obtained: $10^2$ *Escherichia coli* in 1000 ml of water become fixed to the beads of magnetic gel; similarly, the results regarding the specificity of the precipitation by the sera are as good as for *V. cholerae.*

As is apparent from the foregoing text, the detection process according to the invention makes it possible to diagnose the presence of pathogenic germs in less than 48 hours, whereas the same detection by a bacteriological method requires at least 4 days. Moreover, the detection process requires very much less equipment and its cost is low. The quantities of biological medium which it requires are small, as are the quantities of reagents used. Furthermore, starting from only one sample of biological medium, it makes it possible to identify several pathogenic germs which may be present in the sample, using magnetic beads to which different antibodies are coupled, according to the germ to be detected, and corresponding different sera placed in the wells scooped out in the agar.

As is apparent from the foregoing text, the invention is in no way limited to the methods for putting it into effect, the embodiments and the methods of application which have now been described more explicitly; on the contrary, it includes all the variants thereof which may occur to those skilled in the art, without exceeding the framework or the scope of the present invention.

What is claimed is:

1. A process for the immunobacteriological detection of pathogenic germs possessing specific antigenic determinants, in biological media supposedly contaminated by such pathogenic germs, with the aid of a magnetic gel to which are coupled anti-specific antigenic determinant antibodies, which process is characterized by the following steps:
   (a) a biological medium supposedly contaminated by a pathogenic germ possessing a specific antigenic determinant is brought into contact with particles of the magnetic gel to which the said antibodies are coupled for a sufficient time to permit the fixing to the gel of the pathogenic germs possessing the said antigenic determinants contained in the biological medium;
   (b) the particles of magnetic gel are then removed from the mixture by magnetic means and
   (c) are inoculated onto a nutrient agar medium,
   (d) the agar medium containing the magnetic particles is incubated to develop culture colonies of the pathogenic germs;
   (e) areas containing serum containing antibodies specific to the pathogenic germ to be detected are then formed in the agar in the vicinity of the magnetic particles covered with culture colonies, embedded in the agar,
   (f) the germs are lysed by means of lysing agents,
   (g) the lysate is incubated with the serum for a time enabling the serological antibody-antigen reaction to take place by immunodiffusion on the agar, and to form a precipitation band, and
   (h) the quantity of germs contained in the biological medium is read directly, by virtue of the antigen-antibody reaction on the agar.

2. The process as claimed in claim 1, wherein the specific antigenic determinant consists of the antigenic fraction 1+2.

3. The process as claimed in claim 1 or claim 2, wherein in step (e) the areas containing suitable serum containing antibodies specific to the pathogenic germ to be detected are formed by scooping out wells in the agar, and the wells are filled with the same serum.

4. The process as claimed in claim 1, wherein in step (e) the areas containing suitable serum containing antibodies specific to the pathogenic germ to be detected are formed by arranging small discs of paper, impregnated with the same serum, in the vicinity of the magnetic beads covered with culture colonies, embedded in the agar.

5. The process as claimed in claim 1 or claim 2, applied to the simultaneous detection of several different pathogenic germs, wherein in step (e) the areas containing serum containing antibodies specific to the pathogenic germs to be detected, formed in the agar, contain different sera containing antibodies specific to the different pathogenic germs.

6. The process as claimed in claim 1 or claim 2, wherein the said antibodies coupled to the magnetic gel are antibodies for the specific antigenic determinants, originating from a hyperimmune serum containing antibodies specific to the specific antigenic determinants, and obtained by extraction of the IgG from the said hyperimmune serum.

7. The process as claimed in claim 6, for application to the simultaneous detection of several pathogenic germs in a biological medium, wherein series of particles of magnetic gel, each of which has fixed to it said antibodies for the specific antigenic determinants, originating from cultures of each of the pathogenic germs to be detected, are brought into contact with the said biological medium.

8. The process as claimed in claim 5, wherein in step (e) the serum containing antibodies specific to the pathogenic germ, contained in the areas formed in the agar, is selected from the group consisting of sera specific for germs possessing specific antigenic determinants, polyvalent sera containing antibodies specific to pathogenic germs possessing a specific antigenic determinant, sera containing antibodies specific to the toxin of the pathogenic germ, and sera containing antibodies specific to sub-unit A or B of the toxins of the said pathogenic germs.

9. The process as claimed in claim 1 or claim 2 wherein the biological medium to which the process is applied is selected from the group consisting of stools, blood, urine, excretions of all kinds, and water.

10. The process as claimed in claim 1, wherein in step (b) the magnetic means used to remove the particles of magnetic gel from the biological medium, after incubation with the latter, consist of a magnetized rod.

11. The process as claimed in claim 1, wherein the agent in step (f) for lysing the germs cultured on the magnetic particles embedded in the agar is a chemical lysing agent selected from the group consisting of toluene, a condensation product of ethylene oxide with a "Span" detergent formed from fatty acid esters and sorbitol, and glucose.

12. The process as claimed in claim 1, wherein the agent in step (f) for lysing the germs cultured on the magnetic particles embedded in the agar is an enzymatic lysing agent.

13. The process as claimed claim 1 or claim 2, wherein the particles of magnetic gel attached to the magnetic means in step (b) are washed several times before being innoculated onto the agar.

14. The process as claimed in claim 1 or claim 2, wherein the particles of magnetic gel, attached to the magnetic means in step (c) are detached from the latter by the action of a magnetic field in order to be innoculated onto the paper.

15. The process as claimed in claim 1 or claim 2, wherein the contact time in step (a) between the particles of magnetic gel to which said antibodies for the specific antigenic determinants are coupled is about 2 hours at ambient temperature, and the particles are beads.

16. The process as claimed in claim 1 or claim 2, wherein the culture time in step (d) on agar of the germs fixed to the particles of magnetic gel is of the order of 14 to 18 hours at 37° C.±°C., and the mangetic gel particles are beads.

17. The process as claimed in claim 1 or claim 2, wherein in step (e) the areas containing serum containing antibodies specific to the pathogenic germ to be detected are formed by scooping out wells in the agar, and the wells are filled with the said serum and the reaction time in step (g) of the antibodies of the serum contained in the wells inhibiting specific antigenic determinants with the antigens, by immunodiffusion, is of the order of 14 or 18 hours at ambient temperature, and the magnetic gel particles are beads.

18. A ready-to-use kit for carrying out the process as claimed in claim 1, which comprises:
   a receptable containing a suitable quantity of beads of magnetic gel to which an antibody for a specific antigenic determinant is coupled,
   an insulated, magnetized rod,
   a culture dish, the bottom of which is provided with a magnet in the center of its outer face, said magnetic being sufficiently powerful to detach said beads of magnetic gel from said magnetized rod when the beads have been attached to the rod,
   a receptacle containing a quantity of agar medium for the culture of pathogenic germs possessing a specific antigenic determinant,
   a receptacle containing a quantity of serum containing antibodies specific to the pathogenic germ to be detected,
   a receptacle containing a quantity of agents for lysing the cultures of pathogenic germs on agar, and
   a receptacle containing a quantity of buffered physiological wash water.

19. The kit as claimed in claim 18, which comprises an antibody inhibiting fraction 1+2 as the antibody inhibiting specific antigenic determinants.

20. The ready-to-use kit as claimed in claim 18 or 19, which can be applied to the simultaneous detection of several pathogenic germs in a biological medium, which comprises several receptacles each containing a suitable quantity of beads of magnetic gel to which different antibodies for specific antigenic determinants are coupled, and several receptacles each containing a serum containing antibodies specific to the pathogenic germ to be detected corresponding to each of the different antibodies.

21. The process of claim 12 wherein the enzymatic lysing agent is complement.

* * * * *